(12) United States Patent
Szabowski et al.

(10) Patent No.: US 7,998,737 B2
(45) Date of Patent: Aug. 16, 2011

(54) CELL CULTURE OF KERATINOCYTES UNDER NON-DIFFERENTIATING CONDITIONS

(75) Inventors: Axel Szabowski, Wadgassen (DE); Peter Angel, Edingen-Neckarhausen (DE); Julia Knebel, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 12/440,891

(22) PCT Filed: Sep. 7, 2007

(86) PCT No.: PCT/EP2007/059374
§ 371 (c)(1),
(2), (4) Date: Mar. 11, 2009

(87) PCT Pub. No.: WO2008/031767
PCT Pub. Date: Mar. 20, 2008

(65) Prior Publication Data
US 2009/0280095 A1 Nov. 12, 2009

Related U.S. Application Data

(60) Provisional application No. 60/825,355, filed on Sep. 12, 2006.

(51) Int. Cl.
*C12N 5/00* (2006.01)
*C12N 5/07* (2010.01)
*C12N 5/071* (2010.01)
*C12N 15/11* (2006.01)
*C07K 16/00* (2006.01)
*C07K 16/18* (2006.01)
*C07K 16/22* (2006.01)
*C07K 16/24* (2006.01)

(52) U.S. Cl. ........ 435/325; 435/366; 435/371; 435/375; 435/377; 530/387.1; 536/23.1

(58) Field of Classification Search ................... None
See application file for complete search history.

(56) References Cited

U.S. PATENT DOCUMENTS
6,669,938 B1 * 12/2003 Rosenblum et al. ....... 424/183.1

FOREIGN PATENT DOCUMENTS
WO    WO-99/40107 A2    8/1999
WO    WO-2004/106500 A1    12/2004

OTHER PUBLICATIONS

Wille, Jr. et al., "Integrated Control of Growth and Differentiation of Normal Human Prokeratinocytes Cultured in Serum-Free Medium: Clonal Analyses, Growth Kinetics, and Cell Cycle Studies", Journal of Cellular Physiology, vol. 121, pp. 31-44, Alan R. Liss, Inc., 1984.

Jensen et al., "Changes in basal cell subpopulations and tissue differentiation in human epidermal cultures treated with epidermal cultures treated with epidermal growth factor and cholera toxin", Virchows Arch [Cell Pathol], vol. 49, pp. 325-340, Springer-Verlag, 1985.

Price et al., "Approaches to Enhance Proliferation of Human Epidermal Keratinocytes in Mass Culture", vol. 70, No. 5, JNCI, pp. 853-861, 1983.

O'Keefe et al., "Stimulation of Growth of Keratinocytes by Basic Fibroblast Growth Factor", The Journal of Investigative Dermatology, Rapid Communications, pp. 767-769, The Society for Investigative Dermatology, Inc. ,1988.

Van Den Wijngaard et al., "Genomic Organization of the Human Bone Morphogenetic Protein-4 Gene: Molecular Basis for Multiple Transcripts", Biochemical and Biophysical Research Communications, vol. 219, No. 0312, pp. 789-794, Academic Press, Inc., 1996.

Dawson et al., "Pigment Epithelium-Derived Factor: A Potent Inhibitor of Angiogenesis", Science, vol. 285, pp. 245-248, 1999.

Doll et al., "Pigment epithelium-derived factor regulates the vasculature and mass of the prostate and pancreas", Nature Medicine, vol. 9, No. 6, pp. 774-780, Nature Publishing Group, 2003.

Botchkarev et al., "BMP signaling in the control of skin development and hair follicle growth", Differentiation, vol. 72, pp. 512-526, International Society of Differentiation, 2004.

Alberdi et al., "Binding of Pigment Epithelium-derived Factor (PEDF) to Retinoblastoma Cells and Cerebellar Granule Neurons: Evidence for a PEDF Receptor", The Journal of Biological Chemistry, vol. 274, No. 44, pp. 31605-31612, Laboratory of Retinal Cell and Moleclar Biology, 1999.

Volpert et al., "Inducer-stimulated Fas targets activated endothelium for destruction by anti-angiogenic thrombospondin-1 and pigment epithelium-derived factor", Nature Medicine, vol. 8, No. 4, pp. 349-357, Nature Publishing Group, 2002.

Weber et al., "Deletion Mutants of BMP Folding Variants Act as BMP Antagonists and Are Efficient Inhibitors for Heterotopic Ossification", Journal of Bone and Mineral Research, vol. 18, No. 12, pp. 2142-2151, American Society for Bone and Mineral Research, 2003.

Cui et al., "The activity and signaling range of mature BMP-4 is regulated by sequential cleavage at two sites within the prodomain of the precursor", Genes & Development, vol. 15, pp. 2797-2802, Cold Spring Harbor Laboratory Press, 2001.

(Continued)

Primary Examiner — Elizabeth C Kemmerer
(74) *Attorney, Agent, or Firm* — Birch, Stewart, Kolasch & Birch, LLP

(57) ABSTRACT

The present invention relates to a cell culture medium comprising (a) an inhibitor of bone morphogenetic protein-4 (BMP-4) and (b) an inhibitor of pigment epithelium-derived factor (PEDF, also known as SerpinF1). In one embodiment, the inhibitors are antibodies against BMP-4 and PEDF, respectively. The medium allows to culture keratinocytes under non-differentiating conditions. The invention also relates to corresponding methods and kits. As the media and methods disclosed allow for an improved manufacture of keratinocytes, the invention also relates to the treatment of skin wounds and to the manufacture of corresponding medicaments. This will be of advantage for treatment e.g. of burns, ulcers, etc., in which transplantation of keratinocytes or skin is required.

15 Claims, 1 Drawing Sheet

OTHER PUBLICATIONS

Figure 1:
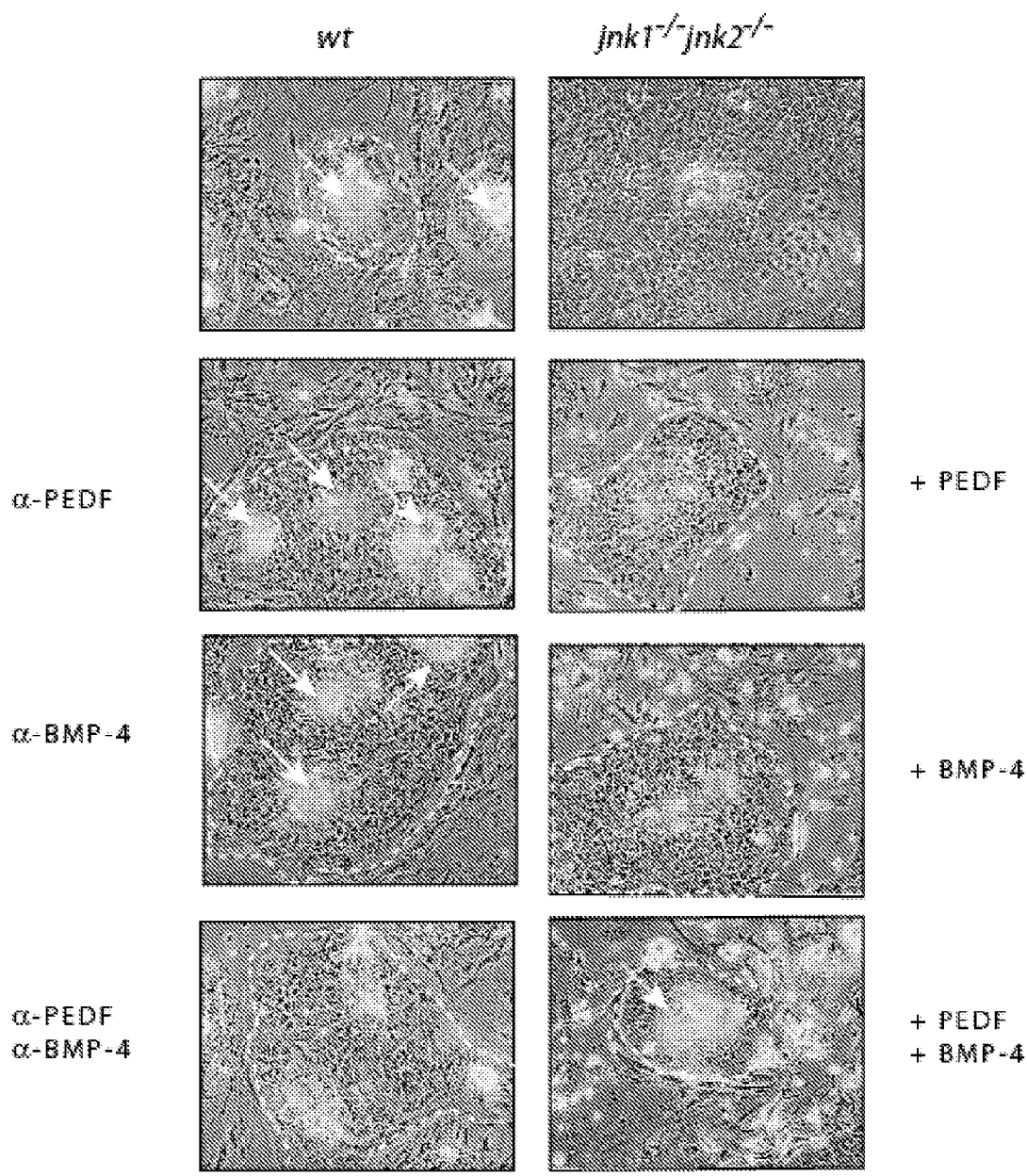

Stark et al., "Organotypic cocultures as skin equivalents: A complex and sophisticated in vitro system", Biol. Proceed. Online, vol. 6, No. 1, pp. 55-60, 2004.

Bell et al., "Living Tissue Formed in vitro and Accepted as Skin-Equivalent Tissue of Full Thickness", Science, vol. 211, pp. 1052-1054, AAAS, 1981.

Greenberg et al., "In Vivo Transplantation of Engineered Human Skin", Methods in Molecular Biology, vol. 289, pp. 425-429, 289, Humana Press Inc., 2005.

Jiao et al., "An essential role of Bmp4 in the atrioventricular septation of the mouse heart", Genes & Development, Research Communication, vol. 17, pp. 2362-2367, Cold Spring Harbor Laboratory Press, 2003.

Horch et al., "Tissue engineering of cultured skin substitutes", J. Cell. Mol. Med., vol. 9, No. 3, pp. 592-608, Department of Plastic and Hand Surgery, University of Erlangen, Nurnberg, Germany, 2005.

Maas-Szabowski et al., "Organotypic Cocultures with Genetically Modified Mouse Fibroblasts as a Tool to Dissect Molecular Mechanisms Regulating Keratinocyte Growth and Differentiation", Journal of Investigative Dermatology, vol. 116, No. 5, pp. 816-820, The Society for Investigative Dermatology, Inc., 2001, XP-002174999.

Coraux et al., "Reconstituted Skin from Murine Embryonic Stem Cells", Current Biology, vol. 13, No. 10, pp. 849-853, Elsevier Science Ltd., 2003, XP-002295445.

Aberdam, D., "Derivation of keratinocyte progenitor cells and skin formation from embryonic stem cells", Int. J. Dev. Biol., vol. 48, pp. 203-206, UBC Press, 2004, XP009036102.

Ek et al., "Pigment epithelium-derived factor: a multimodel tumor inhibitor", Mol. Cancer Ther., vol. 5, No. 7, pp. 1641-1646, Department of Orthopaedics, University of Melbourne, St. Vincent's Hospital and Bone and Soft Tissue Sarcoma Service, Peter MacCallum Cancer Institute, Melbourne, Australia, 2006, XP-002457590.

Dotto, G., "Signal Transduction Pathways Controlling the Switch Between Keratinocyte Growth and Differentiation", Crit. Rev. Oral Biol. Med., vol. 10, No. 4, pp. 442-457, Cutaneous Biology Research Center, Massachusetts General Hospital and Harvard Medical School, Charlestown, Massachusetts, 1999, XP-002457591.

* cited by examiner

CELL CULTURE OF KERATINOCYTES UNDER NON-DIFFERENTIATING CONDITIONS

This application is the National Phase of PCT/EP2007/059374 filed on Sep. 7, 2007, which claims priority under 35 U.S.C. 119(e) to U.S. Provisional Application No. 60/825,355 filed on Sep. 12, 2006, the entire contents of which are hereby expressly incorporated by reference into the present application.

The present invention relates to the culture of keratinocytes, particularly to the culture of keratinocytes under non-differentiating conditions. In particular, the present invention relates to suitable cell culture media and feeder cells. The present invention also relates to the treatment of skin wounds and other diseases associated with the skin.

Keratinocytes are cells present in the epidermis, which is the outer part of the skin. The skin is composed of the so-called epidermis, an external epithelial component, and the so-called dermis, the underlying connective tissue component. The epidermis itself is primarily composed of keratinocytes which are arranged in stratified layers. The so-called stratum basale at the dermal-epidermal junction is a single layer of keratinocytes with a small number of interspersed melanocytes. The stratum basale is also known to the person skilled in the art as stratum germinativum since it is the site of the generation of new keratinocytes by cell proliferation.

Keratinocytes have recently gained importance e.g. in the treatment of skin wounds. Keratinocytes can be transplanted onto skin wounds in order to facilitate the healing process.

In order to obtain a sufficient number of keratinocytes for transplantation onto a wound, it is preferable to cultivate and proliferate the keratinocytes in vitro before transplantation. However, using currently available culture methods, keratinocytes tend to differentiate very quickly. This quick differentiation interferes with sufficient proliferation of the keratinocytes, as terminally differentiated cells do not divide anymore. Thus, it has been difficult to obtain a sufficient number of keratinocytes for transplantation. This is particularly important if the amount of material from which the keratinocytes can be obtained (i.e. a skin biopsy) is limited, e.g. in the case of autologous keratinocytes (i.e. if the keratinocytes are obtained from the patient himself and not from a different donor).

In the state of the art, it has been attempted to obtain a higher number of non-differentiated keratinocytes by pushing primary keratinocytes into proliferation and consequently changing the balance between proliferating and differentiating keratinocytes For example, Wille et al. describe in J. Cell. Physiol., 1984, vol. 121, pages 31-44 that a combination of high EGF and low calcium promote proliferation whereas low EGF and high calcium shifts the balance towards differentiation. Further examples have been disclosed by Jensen et al. regarding EGF and cholera toxin, by Price et al. regarding $Ca^{2+}$ concentrations, and by O'Keefe et al. regarding the use of basic fibroblast growth factor (Jensen, P. K. A., Norgard, J. O. R., and Bolund, L. (1985). Changes in basal subpopulations and tissue differentiation in human epidermal cultures treated with epidermal growth factor and cholera toxin. Virchows Archiv B, vol. 49, pp. 325-340; Price, F. M., Taylor, W. G., Camalier, R. F., et al. (1983). Approaches to enhance proliferation of human epidermal keratinocytes in mass culture. J Natl Cancer Inst., vol. 70 (5), pp. 853-61; O'Keefe, E. J., Chiu, M. L., Payne, R. E. Jr. (1988). Stimulation of growth of keratinocytes by basic fibroblast growth factor. J Invest Dermatol., vol. 90 (5), pp. 767-9).

However, such monoculture conditions do not only change the balance between proliferating and differentiating keratinocytes, but also appear to change the behaviour of the primary cells over time. The changes resemble an increasing independence of cytokines in order to proliferate, which can be interpreted as a first step towards immortilization. Therefore, most experiments with primary keratinocytes are carried out within 6 to 8, but generally within 3 passages, such limitation is a disadvantage if a large number of keratinocytes needs to be generated.

International patent application WO 2004/106500 describes a method for cultivating keratinocytes and increasing the yield of proliferating keratinocytes by using fibroblasts (as feeder cells) the JNK activity of which is eliminated or decreased. This can be achieved for example by eliminating the responsible genes (gene knock-out). However, eliminating genes is not advantageous if feeder cells and keratinocytes are to be derived from the same subject, e.g. a patient. Gene knock-out in such cells is time-consuming and may delay the availability of the keratinocytes for treatment.

Consequently, there is a need to improve the culture of keratinocytes, more particularly, there is a need to provide a method to culture and proliferate keratinocytes without altering their behaviour and abilities, in particular without differentiation.

The problem is solved by a cell culture medium comprising:
a) an inhibitor of bone morphogenetic protein-4 (BMP-4) and
b) an inhibitor of pigment epithelium-derived factor (PEDF).

In the context of the present invention, it has been found that terminal differentiation of keratinocytes can be inhibited, if the keratinocytes are cultured in the absence of BMP-4 and PEDF. BMP-4 and PEDF are typically secreted by cells present in the culture, particularly by so-called feeder cells. Unexpectedly, it was found that the activity of two factors has to be inhibited and that not only one factor is responsible for promoting terminal differentiation of keratinocytes.

The term "cell culture" is known by the person skilled in the art. Particularly, the term "cell culture" relates to cells growing outside the organism in a cell culture medium. The term also relates to the process of growing cells in culture outside the organism.

The term "cell culture medium" is known by the person skilled in the art. In particular, the term "cell culture medium" relates to a medium suitable for growing cells outside the organism. Such media are known to the person skilled in the art and are commercially available. They may comprise nutrients, salts, growth factors, antibiotics, serum (e.g. fetal calf serum) and pH-indicators (e.g. phenol red).

More specific examples of cell culture media are given elsewhere in this specification.

Bone morphogenetic protein 4 (BMP-4) is known to the person skilled in the art. Information is available e.g. at Online Mendelian Inheritance in Man (OMIM), "BMP4", identifier number 112262, see OMIM at the website of the National Center for Biotechnology Information hosted by the National Institutes of Health website, www.ncbi.nlm.nih.gov). BMP-4, the corresponding gene and orthologues from many species are known, e.g. the human gene has been described by Wijngaard, A. et al. (van den Wijngaard A., van Kraay, M., van Zoelen, E. J. J. et al. (1996) Genomic Organization of the Human Bone Morphogenetic Protein-4 Gene: Molecular Basis for Multiple Transcripts. Biochem. Biophys. Res. Commun., vol. 219, pp. 789-794).

Pigment epithelium-derived factor (PEDF, also known as SERPINF1) is known to the person skilled in the art. Information about PEDF is available e.g. at the website Online Mendelian Inheritance in Man, "PEDF", identifier number 172860, see citation above. PEDF has been described by Dawson et al. (Dawson, D. W., Volpert, O. V., Gillis, P., Crawford, S., Xu, H. J. et al. (1999). Pigment epithelium-derived factor: a potent inhibitor of angiogenesis. Science, vol. 285, pp. 245-248). Orthologues of PEDF have also been described, e.g. in mice (Doll, J. A., Stellmach, V. M., Bouck, N. P., Bergh, A. R. J., et al. (2003). Pigment epithelium-derived factor regulates the vasculature and mass of the prostate and pancreas. Nature Med., vol. 9, pp. 774-780), rat, and chicken, see e.g. the HomoloGene tool at the website of the National Center for Biotechnology Information hosted by the National Institutes of Health website, www.ncbi.nlm.nih. gov).

BMP-4 and PEDF are secreted soluble signalling molecules, which exert their biological activity by binding to receptors on the target cell.

Basic mechanisms of BMP signaling are known and have been described (see e.g. Botchkarev and Sharov (2004). BMP signaling in the control of skin development and hair follicle growth; Differentiation, vol. 72, pp. 512). BMP signaling is activated through the binding of ligands to the transmembrane receptor complex formed by type I and type II receptors. Ligand binding to the BMP receptor complex results in phosphorylation of the intracellular domain of the type I receptor by the type II receptor kinases and leads to the transmission of an intracellular signal through BMP-SMAD and/or BMP-MAPK pathways. In the BMP-SMAD pathway, BMPR1 then in turn phosphorylates intracellular Smad-1, -5 or -8 proteins (receptor activated R-Smads) at their C-terminal domain. These R-Smads from heteromeric complexes with Smad-4 (common-partner Smad or Co-Smad) and translocate into the nucleus to regulate the transcription of BMP-responsive genes.

Also basic mechanisms of PEDF signaling are known and have been described. PEDF binds to a single class of binding sites on retinoblastoma and cerebellar granule cells with Kd values of 1, 7-36 nM and 3.2 nM respectively, indicating that the activity of PEDF might be mediated by its interaction with a single receptor type (Alberdi E, Aymerich M S, Becerra S P (1999)). Binding of pigment epithelium-derived factor (PEDF) to retinoblastoma cells and cerebellar granule neurons. Evidence for a PEDF receptor. J Biol Chem vol. 274 (44), pp. 31605-12). PEDF triggers increased phosphorylation of IkB-alpha, decreased levels of IkB, activation of NFkB, nuclear translocation of p65 (RelA) and increased NFkB binding activity as part of its mechanism to protect immature cerebellar granule cells against apoptosis induced by low $K^+$ (Alberdi et al., 1999, cited above) PEDF signaling appears to lead to changes in expression of genes involved in cell survival. It was shown that PEDF increases the expression of FasL and activates a signal transduction cascade that promotes endothelial cell death (Volpert O V, Zaichuk T, Zhou W, Reiher F, et al. (2002). Inducer-stimulated Fas targets activated endothelium for destruction by anti-angiogenic thrombospondin-1 and pigment epithelium-derived factor. Nat Med, vol. 8 (4), pp. 349-57).

In the following, BMP-4 and PEDF, respectively, are referred to as "the factor", as the following definitions apply correspondingly to BMP-4 as well as to PEDF, except where otherwise stated.

According to the present invention, the term "inhibitor" should be understood in its broadest sense. In particular, the term inhibitor relates to any agent which is capable of inhibiting (i.e. preventing or reducing) a given process or the biological activity of a given factor. Regarding BMP-4 and/or PEDF, the term "biological activity" particularly relates to the ability of BMP-4 and/or PEDF to cause differentiation, particularly terminal differentiation of keratinocytes in vitro. The inhibitor may be capable of inhibiting both BMP-4 and PEDF, or the inhibitor capable of inhibiting BMP-4 may be different from the inhibitor capable of inhibiting PEDF.

Preferably, the inhibitor is exogenous, i.e. it is artificially added to the cell culture medium, directly or indirectly (e.g. by use of cells expressing the inhibitor).

The degree of differentiation can be determined by any method deemed appropriate by the person skilled in the art, for example by measuring the level or the presence or absence of biochemical or molecular markers of differentiation. Such measuring can be carried out, e.g. by quantitative RT-PCR analysis, ELISA-based methods, antibody stainings, in situ hybridization, mass spectrometry or any other method for measuring the amount of presence/absence of RNA or proteins or peptides.

In the pathway of differentiation, keratinocytes first express keratin 5 and 14, then they cease to express keratin 5 and 14 and instead express keratin 1 and 10. During further differentiation, keratinocytes start to express loricrin, and, after further differentiation, filaggrin.

More particularly, a keratinocyte is considered to be differentiated if it expresses Keratin 1 or 10, particularly loricrin, more particularly filaggrin. A keratinocyte is also considered to be differentiated if it does not express keratin 5 and 14. Vice versa, a keratinocyte is considered not to be differentiated, if it does express keratin 5 and 14. A keratinocyte is also considered not to be differentiated if it does not express filaggrin, particularly if it does not express loricrin, more particularly if it does not express keratin 1 or 10.

Keratinocytes expressing loricrin, more particularly keratinocytes expressing filaggrin are considered to be "terminally differentiated" in the sense of the invention. However, the invention allows to increase also the fraction of keratinocytes which do not even express keratin 1 and 10 and/or which express keratin 5 and 14.

The terms "expressing", "not expressing", "absence" and "presence" particularly relate to levels of expression typically detectable by antibody stainings according to methods known in the art, more particularly using the streptavidin-avidin system (available e.g. from Vector Laboratories Inc.)

The inhibitor may be capable of inhibiting the signalling pathway of the respective factor at any point of the signalling pathway, e.g. transcription, translation, maturation, secretion or activity of the factor, binding of the factor to the receptor, signalling by the receptor, and downstream signalling inside the keratinocyte.

Inhibition of signalling by the receptor and downstream signalling in the cell may be achieved e.g. by inhibitors of intracellular signalling molecules. For example, the use of siRNAs directed against Smad-1 Smad-5, or Smad-8, or expressing inhibitory SMADs (e.g. SMAD-6 or SMAD-7 may be contemplated.

In a preferred embodiment, the inhibitor inhibits or is capable of inhibiting the binding of the respective factor to its receptor. Binding of the factor to its respective receptor can be inhibited e.g. if the inhibitor itself binds (covalently or non-covalently) to the factor and/or to the receptor.

Generally, molecules capable of binding to a protein (e.g. BMP-4, PEDF, or their receptors) are known as binders. Such binders are known to the person skilled in the art and include e.g. peptide- or nucleic acid-based binders, e.g. soluble extracellular domains of the respective receptors, as well as antibodies, aptamers (particularly nucleic acid-based aptamers), and spiegelmers.

For example, a binder capable of inhibiting the respective factor can be a dominant-negative variant of the respective factor. Dominant-negative variants can be, for example, deletion mutants or folding variants of the respective factor, which are also known in the art (Weber, F. E., Schmokel, H., Oelgeschlager, M., Nickel, J., et al. (2003) Deletion mutants of BMP folding variants act as BMP antagonists and are efficient inhibitors of heterotopic ossification, J. Bone Miner. Res., vol. 18, pp. 2142-51). For example, a dominant-negative variant may bind to the factor to form a biologically inactive dimer of factor and inhibitor, or it may bind to the receptor but does not elicit an intracellular signal.

There are also naturally occurring inhibitors which are capable of binding BMP-4 (e.g. follistatin, noggin, chordin, and DAN family proteins like gremlin). Other suitable binders may include truncated receptors, particularly extracellular receptor domains, which bind to the respective factor. They act as competitive inhibitors to inhibit binding to the respective receptor. Such truncated receptors can be generated by any method known to the person skilled in the art, e.g. by recombinant expression methods.

In a preferred embodiment, the inhibitor of at least one of the factors comprises or is an antibody, more preferably, the both the inhibitors of BMP-4 and PEDF comprise or are antibodies.

Antibodies are known to the person skilled in the art. According to the invention, the term "antibody" is to be understood in a broad sense and comprises polyclonal, monoclonal and recombinantly produced antibodies, as well as any variant or fragments thereof, for example, Fv-, Fab- and $F(ab)_2$-fragments, which may also occur as single-chain molecules. Antibodies capable of inhibiting the binding of BMP-4 and PEDF to their respective receptors are commercially available and are described in the Example section of this specification.

Aptamers and spiegelmers are commercially available (e.g. Noxxon Pharma AG, Berlin, Germany) and can be designed on demand.

Unless otherwise specified, the manipulations of nucleic acids, polypeptides or proteins can be performed using standard methods of molecular biology and immunology (see, e.g. Maniatis et al. (1989), Molecular cloning: A laboratory manual, Cold Spring Harbor Lab., Cold Spring Harbor, N.Y.; Ausubel, F. M. et al. (eds.) "Current protocols in Molecular Biology". John Wiley and Sons, 1995; Tijssen, P., Practice and Theory of Enzyme Immunoassays, Elsevier Press, Amsterdam, Oxford, New York, 1985).

Preferably, binding of a binder occurs with a dissociation constant Kd of $10^7$ M or higher, more preferably of $10^8$ M or higher, more preferably of $10^9$ M or higher, more preferably of $10^{11}$ M or higher, most preferably of $10^{12}$ M or higher. Preferably, the binding is specific. In the context of the invention, specific binding is understood in the sense that the binding between the inhibitor and the respective factor, or between the inhibitor and the receptor of the respective factor occurs with at least 10-fold affinity, preferably at least 20-fold affinity, more preferably at least 50-fold affinity, most preferably at least 100-fold affinity in comparison to the binding to other proteins, in particular in comparison to the binding to proteins of a structure similar to the respective factor. In the case of BMP-4 such comparison may be carried out against TGF-β, more particularly against BMP-2. In the case of PEDF such comparison may be carried out against angiotensinogen (Akt), more particularly against hurpin (Serpin B13). However, a non-specific binding can be tolerable, if the binding does not interfere with the culture of keratinocytes. Preferably, any non-specific binding does not severely affect the amount of inhibitor available for binding to the respective factor or to the receptor of the respective factor, so that it is possible to inhibit the biological activity of the respective factor.

The person skilled in the art is familiar with methods to determine whether an inhibitor is capable of inhibiting the binding of a factor to its receptor. Such method may comprise the steps of (1) incubating the factor and its receptor in presence of a candidate for an inhibitor and (2) measuring the inhibition of the binding between the factor and the receptor. Preferably, such method is carried out under conditions allowing the binding between factor and receptor in absence of a candidate of an inhibitor. The method may also comprise the steps of (3) incubating the factor and its receptor in absence of a candidate for an inhibitor and (4) comparing the binding between the factor and its receptor in absence vs. presence of the candidate of an inhibitor to detect an inhibition and optionally the degree of inhibition caused be the candidate of the inhibitor. Optionally, the method may comprise one or more washing steps.

For example, the factor and/or receptor may be labeled with a suitable label (e.g. a radioactive isotope such as $^{32}P$ or $^{35}S$, a fluorescent marker such as a fluorescent protein (e.g. GFP) or Cy3 or Cy5, or an enzymatic label such as horseradish peroxidase or alkaline phosphatase), and incubated in presence of the inhibitor. The binding between factor and receptor in absence or presence of an inhibitor can be detected and optionally quantified by measuring the amount and localization of the label (co-localization of factor and receptor or their respective label(s) indicates binding between factor and receptor).

Such study may be carried out in vitro in a cell-free system, for example in solution (e.g. measuring an interaction by fluorescence energy transfer (FRET) between labeled factor and labeled receptor) or by binding factor or receptor so a solid support (e.g. a membrane or bead) and contacting the bound molecule with its unbound counterpart (respective factor or receptor). Such binding study may also be carried out in vitro using cellular assays, e.g. by measuring binding of the factor to its receptor on cells (e.g. keratinocytes) carrying the respective receptor. Such cellular system may also allow to measure an inhibition of the biological activity of the factor may be detected, e.g. an inhibition of differentiation of keratinocytes. Furthermore, a binding study may also be carried out in vitro, e.g. by measuring the distribution of a labeled factor in absence or presence of the inhibitor in living tissue (e.g. of an animal) or in tissue samples (e.g. sections) obtained from such tissue.

In another preferred embodiment, the inhibitor inhibits or is capable of inhibiting transcription, translation, maturation, and/or secretion of the respective factor. Such inhibitor may not act indirectly via inhibition of Jnk1 and 2. Inhibitors of transcription or translation are known to the person skilled in the art and may include suitable antisense molecules or nucleic acid derivatives, e.g. siRNAs, morpholinos, and peptide nucleic acids. Antisense molecules or nucleic acid derivatives according to the present invention can be designed as known to the person skilled in the art. There are also commercially available libraries of siRNAs, and other antisense molecules. Thus, in another preferred embodiment, the inhibitor is capable of inhibiting transcription of at least one gene chosen from the group consisting of genes encoding BMP-4 and PEDF.

Inhibitors of maturation are also known in the art. In particular, it is known that BMP-4 is generated by cleavage from a precursor, proBMP-4, through proteolytic cleavage (Cui, Y, Hackenmiller, R., Berg, L., Jean, F. et al. (2001). The activity and signaling range of mature BMP-4 is regulated by sequential cleavage at two sites within the prodomain of the precursor. Genes Dev 2001, vol. 15, 2797-802).

Preferably, the cell culture medium is suitable or designed for the culture of keratinocytes. Such media are know to the person skilled in the art. A suitable medium for the culture of keratinocytes has also been described in the examples.

Media designed for the culture of keratinocytes are preferably those media which comprise at least one component chosen from the group of insulin, corticosteroids, and cholera toxin. The medium may also comprise at least two components chosen from said group, e.g. insulin and a corticosteroids, insulin and cholera toxin, or a corticosteroids and cholera toxin. Preferably, the medium comprises all three components, i.e. insulin, a cortical steroid, and cholera toxin.

The term corticosteroids is known to the person skilled in the art and any corticosteroid deemed appropriate may be chosen for the medium. Preferably, the corticosteroid is a glucocorticoid or a derivative thereof. Also the term "glucocorticoid" is known to the person skilled in the art. Glucocorticoids may comprise e.g. cortisone, hydrocortisone, prednisone, prednilosone, methylprednilosone, prednylidene, deflazacort, fluocortolone, triamcinolone, dexamethasone, betamethasone. Preferably, the glucocorticoid is hydrocortisone. The concentrations correspond in the case of cholera toxin preferably to $10^{-8}$ to $10^{-12}$ M, more preferably to $10^{-9}$ to $10^{-11}$ M, most preferably to $0.5 \times 10^{-10}$ to $2 \times 10^{-10}$ M. In the case of the corticosteroid, the concentrations correspond preferably to a concentration of hydrocortisone of 0.05 to 10 µg/ml, more preferably 0.1 to 5 µg/ml, most preferably 0.2 to 1 µg/ml, most preferably 0.2 to 0.6 µg/ml. It is apparent to the person skilled in the art, that the concentration of any other corticosteroid can be adapted to approximately the same activity on the maintenance of keratinocytes in culture as the concentrations given for hydrocortisone. In the case of insulin, the concentrations correspond preferably to 0.1 µg/ml to 100 µg/ml, more preferably to 0.5 µg/ml to 50 µg/ml, more preferably to 2 to 10 µg/ml, most preferably to 7 to 8 µg/ml.

The insulin may be any kind of natural or recombinantly produced insulin or variant thereof known to the person skilled in the art. Preferably, such variant has a sequence identity of its amino acid sequence of at least 75%, more particularly 80%, more particularly 90%, most particularly 95% to natural human insulin. Such variants are known from pharmaceutical applications and include e.g. variants with a longer or shorter in vivo half-life as compared to natural human insulin. Such variants may also include insulin obtained from other species than humans, e.g. from other mammals (e.g. pigs).

Cholera toxin is an enterotoxin produced by *Vibrio cholerae* and *Vibrio eltor*. The toxin is a protein consisting of seven subunits. Any variants of cholera toxin deemed to be suitable by the person skilled in the art may be employed in the culture medium. Such variants particularly comprise variants of the subunits with an amino acid sequence identity of at least 75%, more particularly 80%, more particularly 90%, more particularly 95%, most particularly 97% to the corresponding subunit of the cholera toxin produced by *vibrio cholerae*.

The medium may also comprise EGF, and/or adenine. For example, a suitable medium may comprise $10^{-10}$ M cholera toxin, 0.1 ng/ml EGF (preferably recombinant human EGF), 0.4 µg/ml hydrocortisone, 5 µg/ml insulin, and 24 ng/ml adenine. The medium may also comprise antibiotics. The medium may also comprise bovine pituitary extract. An example for a basal medium for the culture of keratinocytes in absence of feeder cells comprises 0.5 µg/ml hydrocortisone, 5 µg/ml insulin, 0.1 ng/ml EGF, 0.4% bovine pituitary extract, as well as biologically effective amounts of gentamicin and/or amphotericin.

Whether a cell culture medium is suitable or designed for the culture of keratinocytes may also be determined from package leaflets or labels in or on the package of such medium, stating whether the medium is suitable or designed for the culture of keratinocytes.

The invention also relates to a cell culture (particularly an organotypic cell culture) or tissue culture comprising a medium as defined in the present specification.

Preferably, the cell culture is an organotypic culture, i.e. it comprises the organized growth of cultured cells in a form resembling a tissue. Organotypic cultures are known and have been described, see e.g. Stark et al., 2004 (Stark, H.-J., Szabowski, A., Fusenig, N. E., Maas-Szabowski, N. (2004). Organotypic cocultures as skin equivalents: A complex and sophisticated in vitro system. Biological Procedures Online, 2004, vol. 6, pp. 55-60).

The term "tissue culture" is known to the person skilled in the art, it relates to the culture of a tissue, particularly skin, more particularly epidermis. Such culture may also be a so-called organotypic culture.

In an example of the organotypic form of the coculture system, human primary keratinocytes are seeded onto a fibroblast-embedded (murine or human fibroblasts) collagen matrix and grow air exposed. Within 10 days keratinocytes resemble a stratified epithelia with the characteristic epidermal structure of human skin. These skin-equivalents are already used in clinical trials (Bell E., Ehrlich, H P., et al. (1981) Science, vol. 211, pp. 1052-4; Greenberg S., Marqulis, A., Garlick, J. A. (2005) Methods Mol Biol, vol, 289, 425-430).

The term "keratinocyte" is known to the person skilled in the art. A keratinocyte is an epidermal cell that synthesizes keratin. Keratin is a fibrous protein rich in cysteine and serves as a structural protein forming intermediate filaments. Keratins are present in horn, hair, nails, and the upper flaky layer of skin. In the epidermis, keratinocytes are continuously proliferating and replaced. They migrate from the stratum basale to the stratum corneum and undergo successive steps of differentiation on their way. The keratinocytes may be of mammalian origin, e.g. obtained from a rodent (e.g. mouse or rat), rabbit, cat, dog, or primate (preferably a human subject). Preferably, the keratinocytes are human keratinocytes. Particularly, the invention allows to cultivate and proliferate primary keratinocytes, i.e. keratinocytes which are not obtained from established, particularly immortalized, cell lines. Preferably, the primary keratinocytes have been directly obtained from a biopsy. Particularly, the present invention allows to cultivate and proliferate autologous keratinocytes, most particularly human autologous primary keratinocytes.

In order to graft keratinocytes on skin wounds, it is desirable to avoid terminal differentiation of the keratinocytes in culture. In particular, terminally differentiated keratinocytes do not proliferate anymore, thereby limiting the amount of keratinocytes available for grafting. Terminal differentiation can be determined by stratification of the keratinocytes in the culture and/or by the use of molecular or biochemical markers as described earlier.

The present invention also relates to a kit comprising (a) an inhibitor of BMP-4, (b) an inhibitor of PEDF, and, optionally, (c) a cell culture medium or a cell culture medium stock solution. The components of the kit may be provided in separate containers, for example, a separate container comprising the inhibitor according to (a), and a separate container comprising the inhibitor according to (b) and a separate container comprising the component according to (c). The components according to (a) and (b) may also be provided in the same container. The components may be provided in any form allowing storage or further use. For example, the inhibitors may be provided in lyophilized form. Similarly, the cell culture medium may be provided ready for use or as a stock solution. The cell culture medium may also be provided as a basal medium requiring further supplements to be added to the basal medium. Typically, a basal medium comprises salts and buffers, typical supplements include calcium, growth factors, hormones and antibiotics. Furthermore, the kit may comprise a user's manual, e.g. containing information about how to obtain the final culture medium from the components of the kit.

The present invention also relates to the use of (a) an inhibitor of BMP-4, and (b) an inhibitor of PEDF, or the use of a cell culture medium or a kit as defined in the present specification for the culture of keratinocytes, preferably human keratinocytes.

The present invention also relates to a method of manufacturing a cell culture medium as defined in the present specification, comprising the steps of (a) providing an inhibitor of BMP-4, (b) providing an inhibitor of PEDF, (c) providing a cell culture medium or a stock solution of a cell culture medium, (d) combining the components as defined in steps (a) to (c).

The culture medium according to the present invention can be manufactured according to any method known to the person skilled in the art, e.g. by adding the respective inhibitors to the medium or by providing cells, which secrete a respective inhibitor into the medium. For example, cells can be genetically modified to secrete the inhibitor, for example to secrete a peptide inhibitor, e.g. a truncated receptor.

The invention also relates to the use of cells, particularly feeder cells, which do not secrete BMP-4 and/or PEDF, in presence of (a) an inhibitor of BMP-4 or (b) an inhibitor of PEDF, for culturing keratinocytes. More particularly the invention also relates to (a) the use of cells, particularly feeder cells, which do not secrete BMP-4, in presence of an inhibitor of PEDF, for culturing keratinocytes and/or to (b) the use of cells, particularly feeder cells, which do not secrete PEDF, in presence of an inhibitor of BMP-4, for culturing keratinocytes.

The invention also relates to a method for culturing or manufacturing keratinocytes, comprising the step of (a) cultivating and/or proliferating a keratinocyte in the presence of a medium comprising an inhibitor of BMP-4 and/or an inhibitor of PEDF, particularly in presence of a medium according to any of the definitions in the specification, and/or in the presence of other cells, particularly feeder cells, which do not secrete BMP-4 and/or PEDF. Optionally, said method may comprise the step of harvesting the cultivated and/or proliferated keratinocytes according to step (a). Said method may be adapted according to any features and preferred embodiments mentioned elsewhere in this specification.

Preferably, said other cells particularly feeder cells) have been modified so as not to secrete BMP-4 and/or PEDF. For example, the other cells can be genetically modified, so as to eliminate expression of at least one of the genes encoding BMP-4 and PEDF. Cells not expressing PEDF can e.g. be obtained from knock-out mice (Doll, J. A., Stellmach, V. M., Bouck, N. P., Bergh, A. R. J., et al. (2003). Pigment epithelium-derived factor regulates the vasculature and mass of the prostate and pancreas. Nature Med., vol. 9, pp. 774-780). Cells not expressing BMP-4 can e.g. be obtained from hypomorphic alleles of BMP-4 or by conditional gene inactivation (Jiao, K., Kulessa, H., Tompkins, K., et al. (2003). An essential role of Bmp4 in the atrioventricular septation of the mouse heart. Genes Dev., vol. 17, pp. 2362-2367). It is possible to combine an inhibitor in the medium with the presence of genetically modified cells, such that neither BMP-4 and/or PEDF are present in the medium in a biologically active amount, particularly in an amount sufficient to cause terminal differentiation of keratinocytes.

Methods for genetic manipulation and modification of any other cells present in the culture are known to the person skilled in the art. For example, gene function can be inhibited by knock-out techniques or by introducing vectors which express e.g. antisense molecules interfering with expression of the relevant gene.

Other cells present in the culture may include any cells not being keratinocytes, for example, other cells present in a skin biopsy or feeder cells introduced into the culture to culture the keratinocytes. Such feeder cells are often used in the context of organotypic cultures. The term "feeder cells" is known to the person skilled in the art. Particularly the term "feeder cells" relates to cells which will die after a certain period of time in culture, e.g. due to prior ionizing irradiation of the cells. This technique allows to culture cells, which feed the keratinocytes with nutrients, but do not interfere with formation of a transplant. The feeder cells can be derived from a different donor than the keratinocytes, and may even be derived from a different species ("heterologous culture"). If the feeder cells are derived from the same species as the keratinocytes, then there is less risk of transferring animal diseases (particularly viruses) into the transplant. In the case of human wound treatment it may be preferred to use feeder cells of the same patient (autologous cells). Advantageously, the present invention allows to use such cells, which do not have to be genetically modified.

On the other hand, the invention may also be used in heterologous context. An advantage in using the heterologous form of the coculture system is the application of genetic modified fibroblasts e.g. knock-out fibroblasts which are already available, e.g. as genetically modified mouse fibroblasts. The application of knock-out fibroblasts changes the fibroblast-derived cytokine profile which then influences keratinocyte behaviour. The heterologous cocultures system enables us to distinguish between fibroblast and keratinocyte-derived factors by using species-specific primers in RT-PCR analysis.

The present invention also relates to a method for the manufacture of a medicament for the treatment of skin wounds, comprising the step of manufacturing keratinocytes according to any of the methods laid out in this specification.

The term "skin wound" is to be understood in its broadest sense. A skin wound particularly relates to any damage to the skin tissue, particularly to the epidermis. The term skin wound includes acute, chronic, therapy refractory as well as traumatic skin wounds. Skin wounds can for example be caused by cuts, scrapes, heat, cold, chemical burn (e.g. strong acids or bases), UV irradiation, ionizing irradiation. Skin wounds may also be secondary to other diseases, e.g. cancer (particularly skin cancer), diabetes, microangiopathy, liver disease (e.g. pruritus due to liver disease), allergies, or psychological stress (e.g. neurodermitis). Examples for skin wounds include burn wounds and ulcers (e.g. ulcers resulting from diabetic skin disease).

The medicament can be manufactured according to any appropriate method. Medicaments comprising keratinocytes are known in the art and have been described in a recent review by Horch et al. (Horch, R. E., Kopp, J., Kneser, U., Beier, J., et al. (2005) Tissue engineering of cultured skin substitutes., J. Cell. Mol. Med., vol. 9, pp. 592-608), which is incorporated herein in its entirety by reference, particularly pages 593-602, most particularly the skin substitute techniques according to Table 3. Said medicament may e.g. a keratinocyte formulation or a tissue or skin substitute comprising keratinocytes.

Preferably, the keratinocytes are formulated into a suitable carrier to allow easier application to a skin wound. For example, the keratinocytes can be combined with fibrin solution, factor XIII and aprotinin. Before transplantation, thrombin and calcium are added to the suspension, in order to form a fibrin mesh work, which can be poured onto the wound. The fibrin mesh work may be obtained by activating fibrinogen with thrombin and calcium. It serves as a wound matrix and guidance for the keratinocytes. The cells may also be applied on a biodegradable or non-biodegradable suitable carrier. For example, a carrier mesh work, such as hydrophilic polyurethane membranes (e.g. Epigard™) or a membrane created from polymers of hyaluronic acid (e.g. Laser Skin™) which can be applied to the wound. The membrane may be microporous, in order to allow permeation of gas and the migration of cells. The cells may also be cultivated on floating microspheres (e.g. Cytodex) which can also be applied to the wound. A suitable transplant may comprise keratinocytes, thrombin solution and a glue protein solution. For example, a suitable transplant may comprise keratinocytes at a concentration of $3-6\times10^6$/ml, thrombin solution (human thrombin 500 units, calcium chloride, 5.88 mg), glue protein solution (human plasma protein fraction (80-120 mg), fibrinogen (70-110 mg), factor XIII (10-50 units), plasma fibronectin (2-9 mg), plasminogen (0.02-0.08 mg), bovine aprotinin (3000 kallidenogenase-inactivator units, corresponding to 100 trypsin-inhibitor units)). The transplant may comprise further additives, such as sodium citrate, sodium chloride, glycine, human albumin, heparin, triton, creatine, and water.

The present invention also relates to any corresponding method of treatment comprising the treating of skin wounds with keratinocytes manufactured according to a method as defined in the present specification.

All references cited in this specification are herewith incorporated by reference with respect to their entire disclosure content and the disclosure content specifically mentioned in this specification.

FIGURES

FIG. 1 shows that primary human keratinocytes in feeder layer cocultures do not enter the program of terminal differentiation and stratify, if the activity of BMP-4 and PEDF is neutralized by addition of respective neutralising antibodies (indicated as "α-PEDF" and "α-BMP-4"). Keratinocyte islands are indicated by a dotted line and signs of stratification are indicated by arrows. As a control, feeder-layer cultures containing JNK-deficient fibroblasts, that do not express BMP-4 and PEDF, are used and supplemented with recombinant BMP-4 (50 ng/ml; R&D Systems), see third row from top; PEDF (100 ng/ml; Chemicon), see second row from top; or a combination of both factors, see bottom row. wt, wild type cells; $jnk1^{-/-}jnk2^{-/-}$, jnk1 and jnk2 double knock-out cells All references cited in the entire description (including the examples) are herewith incorporated by reference with respect to their entire disclosure content and the disclosure content specifically mentioned in this description.

The following example serves to illustrate the invention and is not intended to limit the scope of the invention.

EXAMPLE 1

Cell Culture

Normal human skin keratinocytes (NEK) were derived from adult skin (Smola, H., Thiekotter, G., Fusenig N. E., (1993). Mutual induction of growth factor gene expression by epidermal-dermal cell interaction. J Cell Biol, vol. 122, pp. 417-29; Stark H J, Baur M, Breitkreutz D, et al. (1999). Organotypic keratinocyte cocultures in defined medium with regular epidermal morphogenesis and differentiation. J Invest Dermatol, vol. 112 (5), pp. 681-91). NEK were plated on X-irradiated feeder cells (MEFi, 20 Gy) in FAD medium (DMEM: Hams F12/3:1) with 100 U/ml penicillin, 50 µg/ml streptomycin and supplemented with 5% FCS, 5 µg/ml insulin, 0.1 ng/ml recombinant human EGF, 10-10 M cholera toxin, 10-4 M adenine, and 0.4 µg/ml hydrocortisone (Sigma) (Smola et al., 1993, cited above). Mouse wild type and were isolated from mouse embryos and immortalised according to the 3T3 protocol (Schreiber M, Kolbus A, Piu F, Szabowski A, et al. (1999). Control of cell cycle progression by c-Jun is p53 dependent. Genes Dev, vol. 13 (5), pp. 607-19; Kolbus A, Herr I, Schreiber M, Debatin K M, Wagner E F, Angel P. (2000). c-Jun-dependent CD95-L expression is a rate-limiting step in the induction of apoptosis by alkylating agents. Mol Cell Biol, vol. 20 (2), pp. 575-82). Mouse embryonic fibroblasts (MEF) were grown in DMEM supplemented with 10% FCS (Sigma). Medium containing the following additives was replaced every two day: neutralising antibodies against BMP-4 8 µg/ml (R&D Systems) and against PEDF 8 µg/ml (Upstate Technology); recombinant BMP-4 (50 ng/ml; R&D Systems), recombinant PEDF (100 ng/ml; Chemicon).

Medium:

FAD medium (DMEM: Hams F12/3:1) with 100 U/ml penicillin, 50 µg/ml streptomycin and supplemented with 5% FCS, 5 µg/ml insulin, 0.1 ng/ml recombinant human EGF, 10-10 M cholera toxin, 10-4 M adenine, and 0.4 µg/ml hydrocortisone (Sigma).

Antibodies:

Neutralising antibodies against BMP-4 (8 µg/ml; R&D Systems, catalogue no. AF757) and against PEDF (8 µg/ml; Upstate Technology, catalogue no. 07-280).

Factors:

Recombinant BMP-4 (50 ng/ml; R&D Systems), recombinant PEDF (100 ng/ml; Chemicon).

The invention claimed is:

1. A cell culture medium comprising
   (a) an inhibitor of human bone morphogenetic protein 4 (BMP-4) selected from the group consisting of antibodies, aptamers, spiegelmers, siRNAs and antisense molecules targeted to human BMP-4 and
   (b) an inhibitor of human pigment epithelium-derived factor (PEDF) selected from the group consisting of antibodies, aptamers, spiegelmers, siRNAs and antisense molecules targeted to human PEDF.

2. The cell culture medium according to claim 1, wherein binding of BMP-4 and/or PEDF to their respective receptors is inhibited when cells are cultured in the cell culture medium, wherein the cultured cells express BMP-4 and/or PEDF receptors.

3. The cell culture medium according to claim 1, wherein at least one inhibitor of human BMP-4 and/or human PEDF is chosen from the group consisting of aptamers spiegelmers, and antibodies.

4. The cell culture medium according to claim 3, wherein at least one inhibitor is an antibody.

5. The cell culture medium according to claim 1, wherein transcription, maturation, or secretion of BMP-4 and/or PEDF is inhibited when cells are cultured in the cell culture medium.

6. The cell culture medium according to claim 1, wherein at least one inhibitor of human BMP-4 and/or human PEDF is an antisense molecule or a siRNA.

7. The cell culture medium according to claim 1, wherein transcription of BMP-4 and/or PEDF is inhibited when cells are cultured in the cell culture medium.

8. The cell culture medium according to claim 1 comprising sufficient nutrients to permit keratinocytes to be cultured and/or proliferated in the cell culture medium.

9. A cell culture, organotypic cell culture, or tissue culture comprising a cell culture medium comprising (a) an inhibitor of human bone morphogenetic protein 4 (BMP-4) selected from the group consisting of antibodies, aptamers, spiegelmers, siRNAs and antisense molecules targeted to human BMP-4 and (b) an inhibitor of human pigment epithelium-derived factor (PEDF) selected from the group consisting of antibodies, aptamers, spiegelmers, siRNAs and antisense molecules targeted to human PEDF and cells that have been cultured and/or proliferated in the cell culture medium.

10. A kit comprising (a) an inhibitor of human BMP-4 selected from the group consisting of antibodies, aptamers, spiegelmers, siRNAs and antisense molecules targeted to human BMP-4, (b) an inhibitor of human PEDF selected from the group consisting of antibodies, aptamers, spiegelmers, siRNAs and antisense molecules targeted to human PEDF, and, optionally, (c) a cell culture medium or cell culture medium stock solution.

11. A method of manufacturing a cell culture medium comprising the steps of
  (a) providing an inhibitor of human BMP-4 selected from the group consisting of antibodies, aptamers, spiegelmers, siRNAs and antisense molecules targeted to human BMP-4,
  (b) providing an inhibitor of human PEDF selected from the group consisting of antibodies, aptamers, spiegelmers, siRNAs and antisense molecules targeted to human PEDF,
  (c) providing a cell culture medium or a stock solution of a cell culture medium,
  (d) combining the components as defined in steps (a) to (c).

12. A method for culturing or proliferating keratinocytes, comprising the step of
  cultivating and/or proliferating a keratinocyte in the presence of a medium comprising (a) an inhibitor of human bone morphogenetic protein 4 (BMP-4) selected from the group consisting of antibodies, aptamers, spiegelmers, siRNAs and antisense molecules targeted to human BMP-4 and (b) an inhibitor of human pigment epithelium-derived factor (PEDF) selected from the group consisting of antibodies, aptamers, spiegelmers, siRNAs and antisense molecules targeted to human PEDF, optionally, cultivating and/or proliferating the keratinocyte in the presence of other cells, which do not secrete BMP-4 and/or PEDF.

13. A method for producing keratinocytes suitable for transplantation onto skin wounds, comprising cultivating and/or proliferating a keratinocyte in the presence of a medium comprising (a) an inhibitor of human bone morphogenetic protein 4 (BMP-4) selected from the group consisting of antibodies, aptamers, spiegelmers, siRNAs and antisense molecules targeted to human BMP-4 and (b) an inhibitor of human pigment epithelium-derived factor (PEDF) selected from the group consisting of antibodies, aptamers, spiegelmers, siRNAs and antisense molecules targeted to human PEDF, optionally, cultivating and/or proliferating the keratinocyte in the presence of other cells which do not secrete BMP-4 and/or PEDF.

14. The cell culture medium according to claim 1 comprising:
  (a) an antibody against human bone morphogenetic protein 4 (BMP-4),
  (b) an antibody against human pigment epithelium-derived factor (PEDF), and
  (c) nutrients sufficient to support culturing and/or proliferation of human keratinocytes.

15. The cell culture, organotypic cell culture, or tissue culture according to claim 9, wherein the cells are keratinocytes.

* * * * *